(12) United States Patent
DiCarlo

(10) Patent No.: US 7,799,066 B2
(45) Date of Patent: Sep. 21, 2010

(54) DEVICES AND METHODS FOR AAA MANAGEMENT

(75) Inventor: Paul DiCarlo, Middleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 666 days.

(21) Appl. No.: 11/891,793

(22) Filed: Aug. 13, 2007

(65) Prior Publication Data

US 2007/0282423 A1   Dec. 6, 2007

Related U.S. Application Data

(62) Division of application No. 10/245,034, filed on Sep. 16, 2002, now Pat. No. 7,264,631.

(51) Int. Cl.
  *A61F 2/06* (2006.01)
(52) U.S. Cl. .................................................. 623/1.13
(58) Field of Classification Search ....... 623/1.11–1.14, 623/1.2, 1.23; 606/191–198; 128/898
  See application file for complete search history.

(56) References Cited

U.S. PATENT DOCUMENTS

| | | | |
|---|---|---|---|
| 4,655,771 A | 4/1987 | Wallsten | |
| 5,405,378 A | 4/1995 | Strecker | |
| 5,683,449 A * | 11/1997 | Marcade | 128/898 |
| 6,099,526 A | 8/2000 | Whayne et al. | |
| 6,764,503 B1 | 7/2004 | Ishimaru | |
| 7,344,556 B2 * | 3/2008 | Seguin et al. | 623/1.11 |
| 7,699,885 B2 * | 4/2010 | Leonhardt et al. | 623/1.13 |

FOREIGN PATENT DOCUMENTS

| | | |
|---|---|---|
| EP | 1 097 728 A1 | 5/2001 |
| WO | WO99/33402 | 7/1999 |
| WO | 0002615 A1 | 1/2000 |

OTHER PUBLICATIONS

Japanese Office Action and English Translation dated Feb. 3, 2010 for related Japanese Patent Application No. 2004-536091. 5 pgs.

(Continued)

*Primary Examiner*—Kevin T Truong
(74) *Attorney, Agent, or Firm*—Brooks, Cameron & Huebsch, PLLC

(57) ABSTRACT

A method of treating an abdominal aortic aneurysm is disclosed. The method includes the steps of providing an endovascular graft configured to be disposed within an aorta of a patient and to be attached to an aortic wall to channel aortic blood flow therethrough; advancing a temporary stent catheter endovascularly to a location of the aneurysm, the catheter being attached to a temporary stent, the temporary stent and the graft being constrained by one or more constraining devices during advancement of the graft; removing the one or more constraining devices from the graft and temporary stent, to allow the temporary stent to stabilize the graft against the aortic wall; fixing the graft to the aortic wall; reconstraining the temporary stent with one of the one or more constraining devices; and withdrawing the temporary stent catheter, temporary stent and the one or more constraining devices, releasing the graft.

50 Claims, 8 Drawing Sheets

OTHER PUBLICATIONS

Timothy Baxter, 'Video-assisted Retroperitoneal Approach for Abdominal Aortic Aneurysm', American Journal of Surgery vol. 172, Oct. 1996, pp. 363-365.

William Wisselink, 'Retroperitoneal Endoscopic Ligation of Lumbar and Inferior Mesenteric Arteries as a Treatment of Persistent Endoleak After Endoluminal Aortic Aneurysm', Journal of Vascular Surgery, vol. 31, No. 6, pp. 1240-1244.

L. L. Swanstrom, 'Total :Laparoscopic Abdominal Aortic Aneurysm Repair', Surgical Endoscopy (1999), No. 13, pp. 77-79.

J. Edoga, 'Laparoscopic-assisted Abdominal Aortic Aneurysmectomy', Journal of Vascular Surgery, vol. 32, No. 2, pp. 224-233.

David W. Feigal, Jr., 'FDA Public Health Notification: Problems with Endovascular Grafts for Treatment of Abdominal Aortic Aneurysm (AAA)', Letter, Apr. 27, 2001, pp. 1-3.

Invitation to Pay Additional Fees w/ Search Report Annex, date of mailing Feb. 5, 2004.

Japanese Official Action for related Japanese Application No. 2004-536091. Jun. 4, 2009. 12 pages.

* cited by examiner

DEVICES AND METHODS FOR AAA MANAGEMENT

CROSS REFERENCE TO RELATED APPLICATION

This application is a divisional application of U.S. patent application Ser. No. 10/245,034 (allowed), filed on Sep. 16, 2002 now U.S. Pat. No. 7,264,631.

TECHNICAL FIELD

This invention relates to devices and methods for endovascular delivery and placement of a luminal graft, particularly an endoluminal graft and more particularly to endovascular and/or laparoscopic management of an abdominal aortic aneurysm sac.

BACKGROUND OF THE INVENTION

Abdominal aortic aneurysms (AAA) 12 as shown in FIG. 1 require surgical treatment to prevent rupture of the AAA sac and resulting mortality. The conventional surgical procedure for treatment of an AAA uses a transabdominal or retroperitoneal surgical approach that involves surgically exposing the aneurysm and replacing a diseased aortic segment including the AAA sac with an in-line endograft. The AAA is excluded from pressurized blood flow by clamping the aorta 2 with the use of an aortic prosthesis of appropriate size that is sutured just proximally below the renal arteries and distal to the two iliac arteries 4. The sac is cleaned and back bleeders are treated. A vascular graft is placed in the aorta and sutured proximal and distal the aneurysm. Once the graft is in place, the sac is folded over the graft and sutured and the aorta is unclamped and blood flow is allowed to resume.

The transabdominal or retropariteneal surgical treatment for AAA is highly invasive, requiring a large incision in the abdomen and occlusion of blood flow in the aorta. This treatment has a demonstrated operative mortality rate of about 3 percent for optimally selected patients, and is unfavorable for octogenarians and high-risk patients with multiple disorders. Also, this treatment requires an average hospital stay of about 12 days and a progressive recovery time of months, adding substantially to the cost of the procedure.

Another treatment for AAA involves endovascular placement of a stent-graft 20 to bypass the aneurysm, as shown in FIG. 2. One such stent-graft is disclosed in U.S. Pat. No. 4,655,881, which is incorporated herein by reference. This stent graft comprises co-knitted stent (wire loops) 22 and graft (fabric loops) 24. Such a stent-graft 20 may be introduced intravascularly, typically under fluoroscopic guidance, through an opening formed in an iliac artery in the groin into the abdominal aorta 2 using a delivery catheter. The stent-graft may be radially self-expanding in an unrestrained condition, in which case, it would be constrained during delivery to the location of the aneurysm. The stent-graft may be fixed to the aortic wall proximal and distal the aneurysm 12 by expansion of the stent-graft or by hooks that fixate and seal the proximal and distal attachment sites to the iliac artery and aortic walls, respectively.

Alternatively, the stent-graft may be delivered to the location of the aneurysm and expanded by a balloon. The stent-graft is crimped onto the balloon which is introduced intravascularly through an opening in an iliac artery using a catheter. When the balloon and stent-graft are positioned at the location of the aneurysm, the balloon is expanded by pumping fluid into the balloon. The balloon is then deflated and withdrawn through the iliac artery. It should be noted that both the self-expanding stent-graft and the balloon expanding stent-graft described above are introduced with the blood flow in the aorta interrupted.

The endovascular approach is less traumatic and has demonstrated a lower morbidity rate, quicker recovery, and lower cost than the transabdominal or retroparitenal surgical approach. The endovascular approach has shown promise in treating intrarenal AAA, isolated thoracic aortic aneurysm, and even isolated peripheral traumatic aneurysms. The endovascular approach, however, is compromised by several complications. One such complication is the occurrence of endoleaks. Size and topographical differentials between the stent-graft and the aorta can result in a persistent blood flow outside the lumen of the endovascular stent-graft into the aneurysmal sac following placement of the endovascular stent-graft. Endoleaks can also be caused by incomplete apposition of the attachment sites against the aortic wall. Since pressurized blood flow continues to reach the aneurysmal sac, sac rupture can result. Accordingly these leaks are known as type I endoleaks. Another type of endoleak can occur as a result of the patient's inferior mesenteric artery and lumbar vessels continuing to feed the aneurysmal sac laterally. This type of endoleak has the potential to result in sac rupture. A second complication that can occur with the endovascular approach using a stent-graft is a condition called "stent abrading." Other complications that can occur with the endovascular approach include: balloon malfunction, prosthesis (i.e., stent-graft) migration, stent-graft thrombosis and inadvertent obturation of renal arteries.

To overcome the shortcomings of existing treatments for AAA, a need exists for a minimally invasive and minimally traumatic treatment of AAA that reduces the risks of endoleaks, graft migration, graft thrombosis, obturation of renal arteries, and stent abrading. Comparable problems and needs can be identified in the treatment and devices used for surgical and endoluminal repair of defects in other body lumens.

SUMMARY OF THE INVENTION

To meet these and other needs, and in view of its purposes, an exemplary embodiment of the present invention provides minimally invasive devices and methods for delivering and fixing a graft at a vascular aneurysm or other graft location. In an exemplary embodiment of the invention, a method of treating an abdominal aortic aneurysm is provided. The method comprises the steps of providing an endovascular graft configured to be disposed within an aorta of a patient and to be attached to an aortic wall to channel aortic blood flow therethrough; advancing a temporary stent catheter endovascularly to a location of the aneurysm, the catheter being attached to a temporary stent; the temporary stent being generally tubular and having a distal end and a proximal end and comprising outwardly expanding helically braided thread members, the temporary stent being tapered and affixed to the catheter at the proximal end and terminating in discrete ends temporarily affixed to the graft at the distal end, the temporary stent and the graft being constrained by one or more constraining devices during advancement of the graft; removing the one or more constraining devices from the graft and temporary stent, to allow the temporary stent to stabilize the graft against the aortic wall; fixing the graft to the aortic wall; reconstraining the temporary stent with one of the one or more constraining devices; and withdrawing the temporary stent catheter, temporary stent and the one or more constraining devices, releasing the graft.

The invention further discloses a method of treating a thoracic aortic aneurysm comprising the steps of providing an endovascular graft configured to be disposed within an aorta of a patient and to be attached to an aortic wall to channel aortic blood flow therethrough; advancing a temporary stent catheter endovascularly to a location of the aneurysm, the catheter being attached to a temporary stent, the temporary stent being generally tubular and having a distal end and a proximal end and comprising outwardly expanding helically braided thread members, the temporary stent being tapered and affixed to the catheter at the proximal end and terminating in discrete ends temporarily affixed to the graft at the distal end; the temporary stent and the graft being constrained by one or more constraining devices during advancement of the graft; drawing the one or more constraining devices off of the graft and the temporary stent to allow the temporary stent to stabilize the graft against the aortic wall; fixing the graft to the aortic wall; reconstraining the temporary stent with one of the one or more constraining devices; and withdrawing the temporary stent catheter, temporary stent and constraining devices, releasing the graft.

The invention further discloses a method of treating a luminal defect aneurysm comprising the steps of providing an endoluminal graft configured to be disposed within a body lumen of a patient and to be attached to a luminal wall to channel fluid flow therethrough; advancing a temporary stent catheter endoluminally to a location of the defect, the catheter being attached to a temporary stent, the temporary stent having a radially expanded configuration and a radially compressed configuration and comprising helically braided thread members, the temporary stent terminating in discrete ends temporarily affixed to the graft, the temporary stent being in the radially compressed configuration during advancement of the graft; expanding the sheath to the radially expanded configuration to stabilize the graft against the luminal wall; fixing the graft to the luminal wall; constraining the temporary stent to release the graft; and withdrawing the temporary stent catheter and temporary stent from the patient. It is to be understood that both the foregoing general description and the following detailed description are exemplary, but are not restrictive, of the invention.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Figure 1:
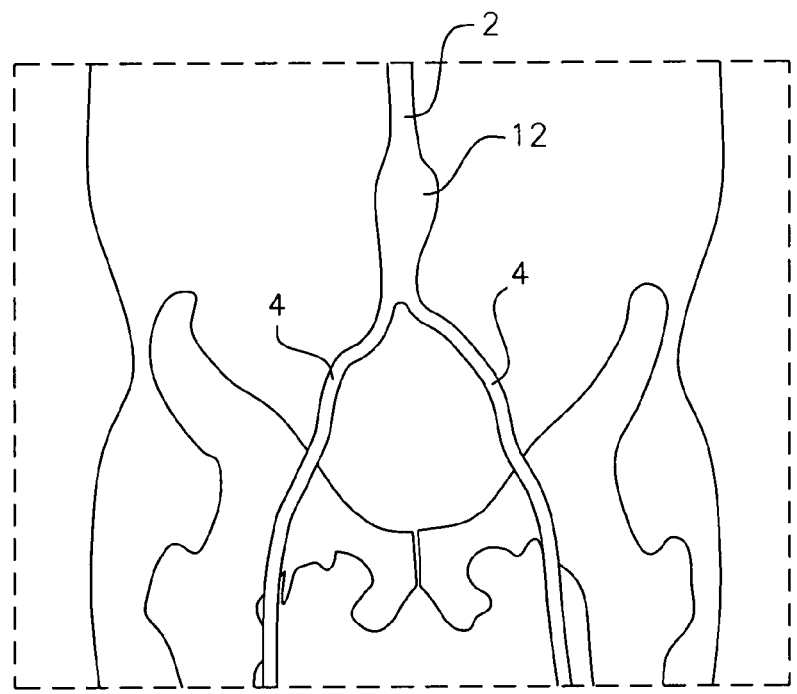
FIG. 1 shows an abdominal aorta with an abdominal aortic aneurysm (AAA), and connecting iliac arteries.
Figure 2:
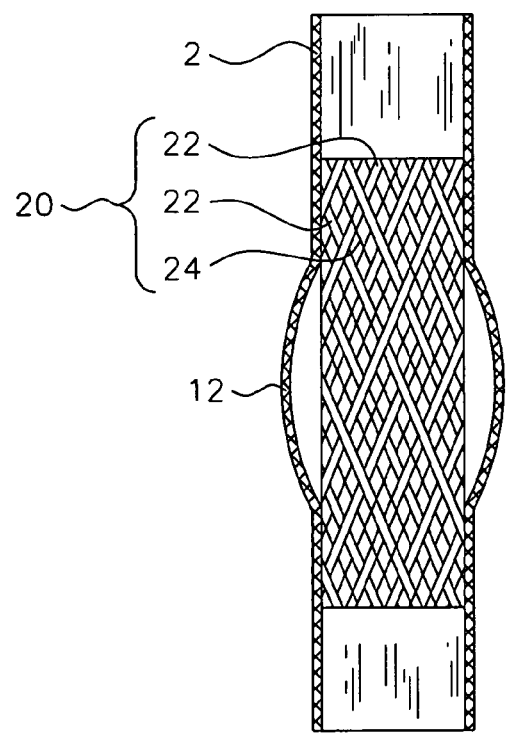
FIG. 2 shows a stent-graft bypassing an enlarged section of a body lumen, such as an abdominal aortic aneurysm.

Referring now to the drawing, in which like reference numbers refer to like elements throughout, FIGS. 3, 4, and 6-11 show an exemplary embodiment of a temporary stent for endovascularly delivering a graft to a location of an abdominal aortic aneurysm and stabilizing the graft during fixation to the aortic wall.

When used herein, the following words and phrases have the meaning provided. Proximal indicates a direction toward an operator of a device or more particularly toward a point of entry into a patient's body. Distal indicates a direction away from an operator of a device, and more particularly, toward a patient's heart. Longitudinal and axial mean in a direction parallel to the axis of a temporary stent, graft, or a blood vessel.

Figure 3:
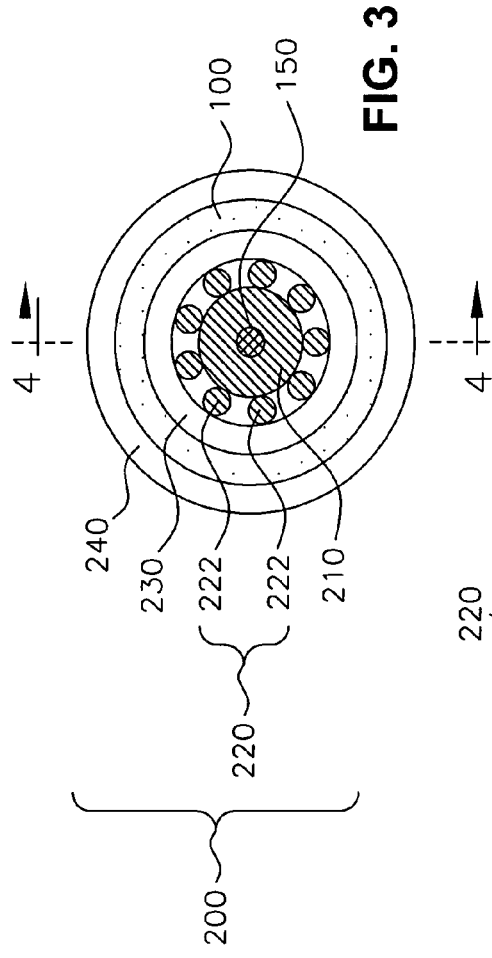
FIG. 3 is a diametrical sectional view of a graft delivery device according to an exemplary embodiment of the invention.
Figure 4:
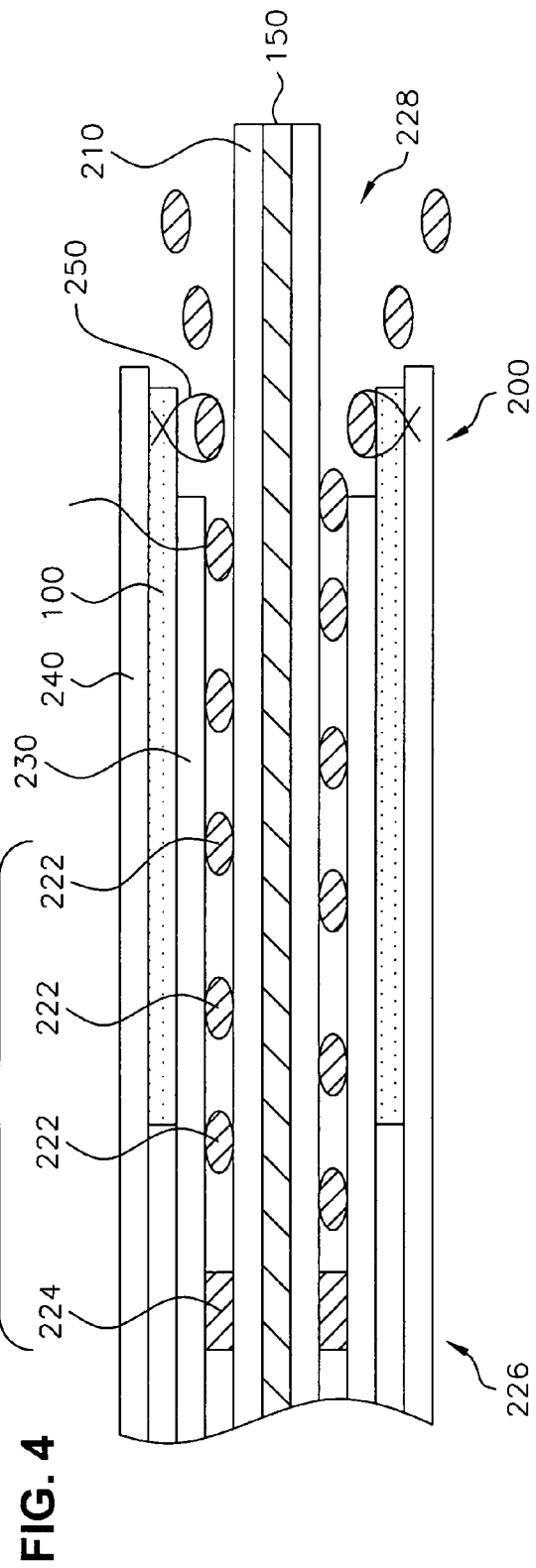
FIG. 4 is a longitudinal sectional view of the delivery device of FIG. 4 taken generally along axis 4-4 in FIG. 3.

Referring now to FIGS. 3 and 4, a temporary stent 220 is used to deliver a graft 100 to a location of an aneurysm (not shown). Graft 100 may be, for example, a stentless fabric graft. As shown in FIGS. 3 and 4, graft 100 is temporarily attached to temporary stent 220 at a distal end 228 of temporary stent 220. In an exemplary embodiment of the invention, graft 100 is temporarily attached to temporary stent 220 by a temporary attachment device 250, which may be, for example, a suture. Alternatively, temporary attachment device 250 may be a bead of adhesive or pockets formed in graft 100. For example, pockets may be formed by folding over the distal end of graft 100 and fixing graft 100 in this configuration, either permanently or temporarily.

Figure 6:
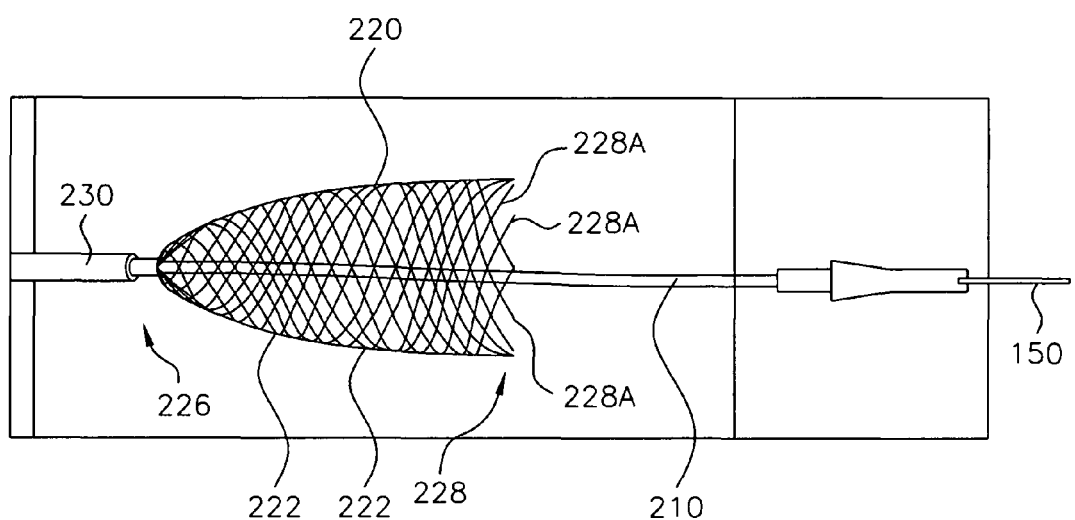
FIG. 6 is a side view of the delivery device of FIG. 3 with the graft and sheath omitted for clarity, and with a delivery or temporary stent in its expanded (unconstrained) configuration.
Figure 7:
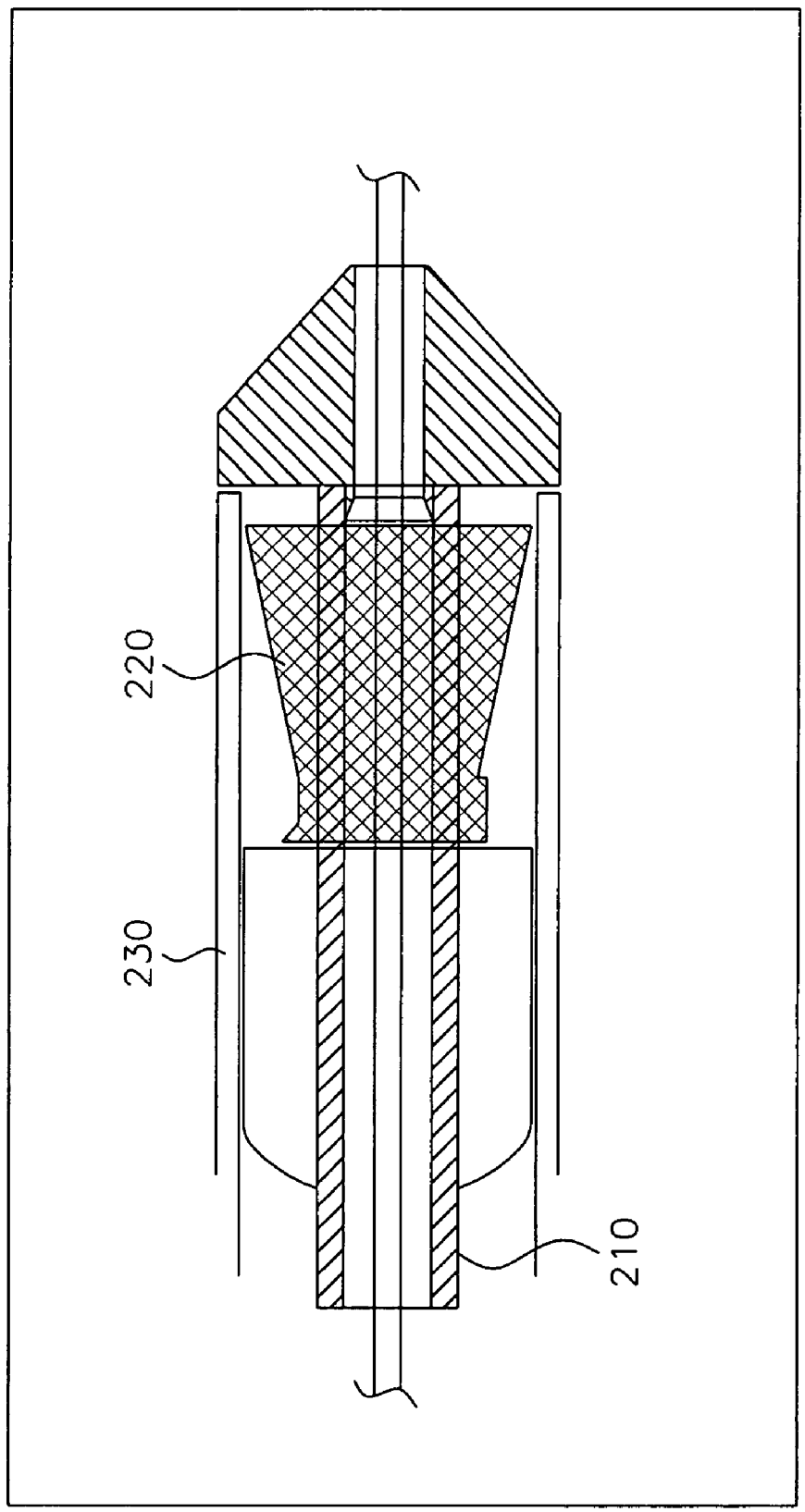
FIG. 7 is a side view of the delivery device of FIG. 3 with the graft omitted for clarity, and with a delivery or temporary stent in a reconstrained configuration.
Figure 8:
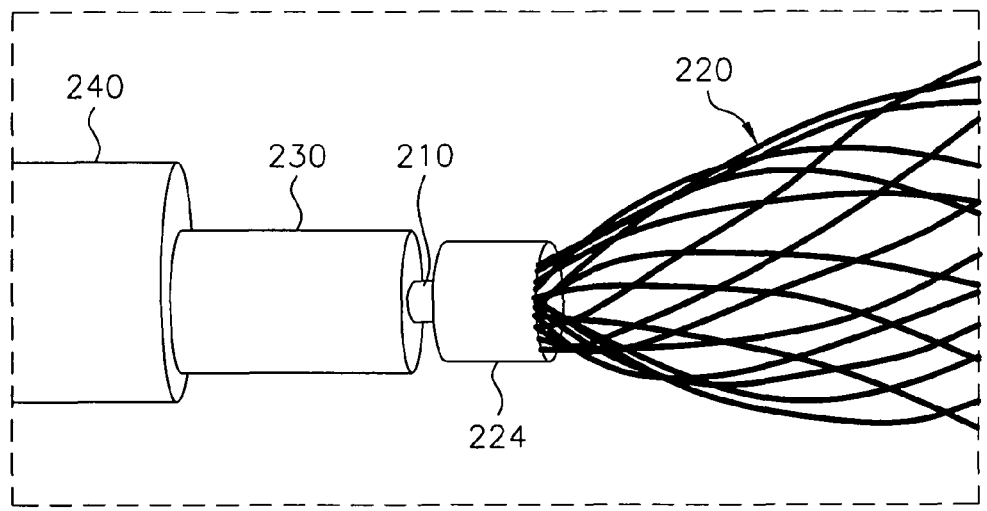
FIG. 8 is a detailed view of the proximal end of the delivery device of FIGS. 4-6 with the graft and sheath omitted for clarity, and with a delivery or temporary stent in its expanded (unconstrained) configuration.

Referring now to FIGS. 6-8, temporary stent 220, is generally tubular in shape, and has a distal end 228 and a proximal end 226. Temporary stent 220 may comprise helically braided thread members 222 that expand radially outwardly to a maximum diameter in a resting state, and terminate at distal end 228 in discrete ends 228A. Braided thread members 222 cross or pass one another at multiple locations along the length of temporary stent 220 forming generally diamond shaped openings or cells bounded by four thread members.

Individual thread members 222 may, for example, alternately pass over then pass under other thread members at these locations. As shown in FIGS. 6 and 7, temporary stent 220 may be tapered at proximal end 226 and open at distal end 228. In an exemplary embodiment of the invention, temporary stent 220 comprises two pluralities of parallel helical thread members 222. The two pluralities cross one another at a multiplicity of intersecting locations along the length of temporary stent 220 and terminate with discrete ends 228A (i.e., ends that are not attached to other thread members), as described in U.S. Pat. No. 4,655,771. Thread members 222 may be captured or retained by a connecting structure 224, as shown in FIG. 8, at an end of the temporary stent opposite discrete ends 228A. Thread members 222 may comprise a material having an elasticity sufficient to cause radial expansion of temporary stent 220, for example, elgiloy. Alternatively, thread members 222 may comprise a material having shape memory causing radial expansion of temporary stent 220, for example, nitinol. Thread members 222 may comprise either a bio-absorbable or a not bio-absorbable material.

Although temporary stent 220 is illustrated and described above comprising helically braided thread members, it should be noted that alternative configurations of temporary stent 220 are contemplated. For example, temporary stent may comprise a continuous helix of connected spirals or hoops of material with a sinuous or zig-zag configuration connected at apices formed by the sinuous or zig-zag configuration. Alternatively, temporary stent may comprise a laser cut nitinol tube, leaving interconnected thread members.

Temporary attachment device 250 (as shown in FIG. 4) attaches graft 100 (shown in FIG. 4) to temporary stent 220 by surrounding thread members, preferably about two cells from discrete ends 228A. Temporary attachment device 250 may comprise, for example, a suture or a bead of adhesive. Temporary attachment device 250 may be bio-absorbable so that it does not remain in the body or not bio-absorbable so that it can provide increased structural integrity.

Temporary stent 220 is affixed to a catheter 210 to form a device 200 for endovascular delivery of a vascular graft to a graft location of a blood vessel. Catheter 210 is a tube having sufficient stiffness to be advanced through blood vessels in a patient's circulatory system and having a lumen therein. Catheter 210 is sized and configured to be advanced through selected blood vessels in a patient's body over a guide wire 150 extending through its lumen to a graft location (e.g., the location of an aneurysm).

In an exemplary embodiment of the invention, delivery device 200 includes a sheath 230 for radially constraining temporary stent 220. Sheath 230 is longitudinally or axially moveable with respect to temporary stent 220, such that it may surround (i.e., be positioned over) and restrain temporary stent 220 in one position as shown in FIGS. 3, 4, and 7. In a different position, as shown in FIG. 6, sheath 230 is axially displaced or withdrawn from temporary stent 220 allowing the temporary stent to expand radially. Sheath 230 has a proximal opening configured such that temporary stent 220 may be reversibly and repeatably captured at tapered distal end 226 to radially constrain and reconstrain temporary stent 220. In an exemplary embodiment, as shown in FIGS. 3 and 4, graft 100 may be disposed radially over sheath 230 during delivery or advancement of graft 100 to the location of an aneurysm.

In the embodiment shown in FIGS. 3 and 4, an outer sheath 240 may be provided to radially restrain graft 100 during delivery or advancement of the graft. Outer sheath 240 is disposed radially overlying graft 100. Outer sheath 240 is longitudinally or axially moveable with respect to graft 100 to allow graft 100 to be radially expanded and stabilized against a wall of a blood vessel. In an exemplary embodiment of the invention, outer sheath 240 is drawn axially off of graft 100. Then sheath 230 is drawn axially off of temporary stent 220, allowing temporary stent 220 to radially expand, causing graft 100 to radially expand against the wall of a lumen or blood vessel to be treated. While sheath 230 and outer sheath 240 are shown as separate structures, alternative embodiments of delivery device 200 are contemplated wherein a single sheath constrains both graft 100 and temporary stent 220, or a sheath constrains temporary stent 220 and graft 100 is constrained by a crochet.

Figure 5:
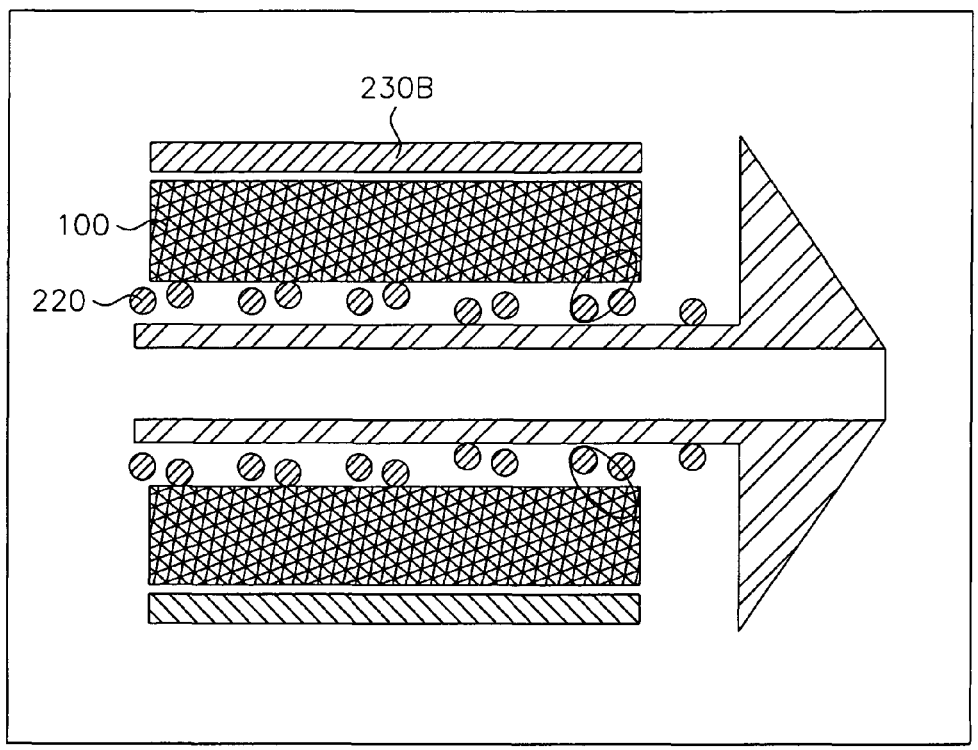
FIG. 5 is a longitudinal sectional view of an alternative delivery device having only an outer sheath that constrains both the graft and the temporary stent.

In one alternative exemplary embodiment of the invention, as shown in FIG. 5, a single sheath 230B is provided radially overlying and selectively restraining both temporary stent 220 and graft 100. In this exemplary embodiment, single sheath 230B is drawn off of graft 100 and temporary stent 220 when the assembly is at the aneurysm location. When single sheath 230B is axially withdrawn, temporary stent 220 radially expands, expanding graft 100. When single sheath 230B is axially advanced following fixation of graft 100, only temporary stent 220 is reconstrained.

Figure 14:
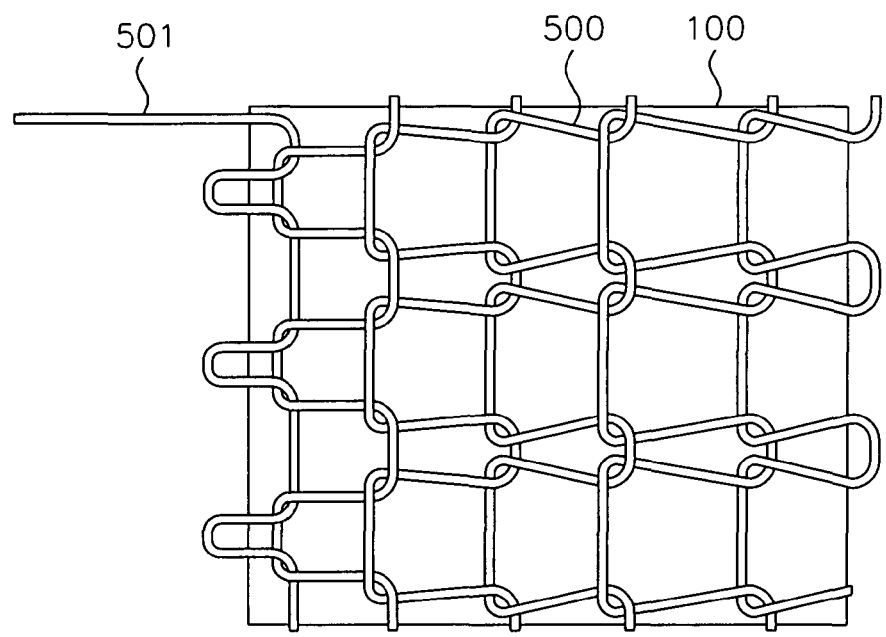
FIG. 14 shows a crochet rip cord for constraining a graft according to an exemplary embodiment of the invention.

Alternatively, graft 100 may be constrained during delivery or advancement by a crochet rip cord 500 as shown in FIG. 14, adapted to permit release of the constraint by pulling the rip cord and unraveling the crochet. An exemplary crochet rip cord is disclosed in U.S. Pat. No. 5,405,388, which is incorporated herein by reference. Crochet rip cord 500 may be stripped by pulling a trailing thread 501, removing the restraining force from temporary stent 220.

Referring again to the exemplary embodiment of the invention shown in FIGS. 3 and 4, sheath 230 is configured to be drawn over temporary stent 220 and outer sheath 240 is drawn over graft 100 during advancement of graft 100. Thus, the radius of the assembled delivery device 200 and graft 100 during delivery or advancement of graft 100 is smaller than the radii of the blood vessels that the assembly is advanced through, facilitating delivery. When graft 100 is advanced to a graft location (i.e., location of an aneurysm), sheath 230 is drawn proximally off of temporary stent 220. As sheath 230 is drawn off of temporary stent 220, temporary stent is allowed to expand, as shown in FIG. 6. In the expanded configuration, temporary stent 220 stabilizes graft 100 against the wall of a blood vessel. Once graft 100 is stabilized, it can be fixed to the blood vessel.

Figure 9:
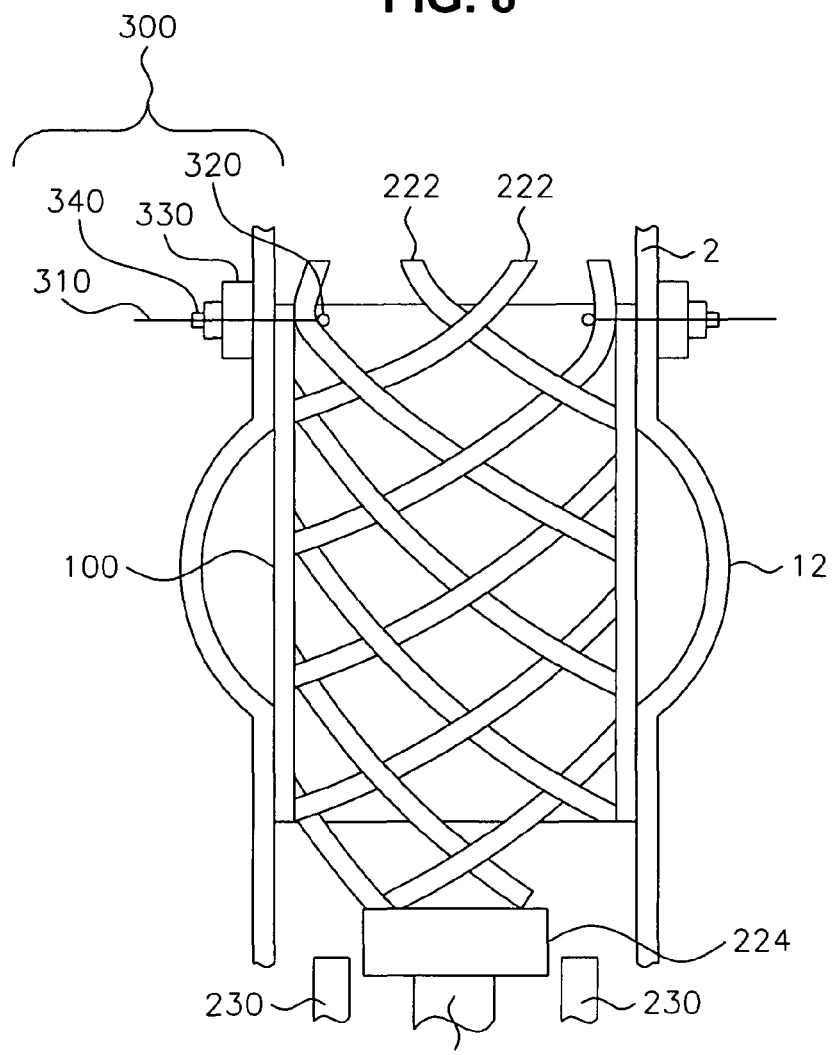
FIG. 9 shows a graft stabilized at an aneurysm (e.g., an abdominal aorta aneurysm) by a reconstrainable temporary stent during fixation of the graft according to an exemplary embodiment of the invention.
Figure 10:
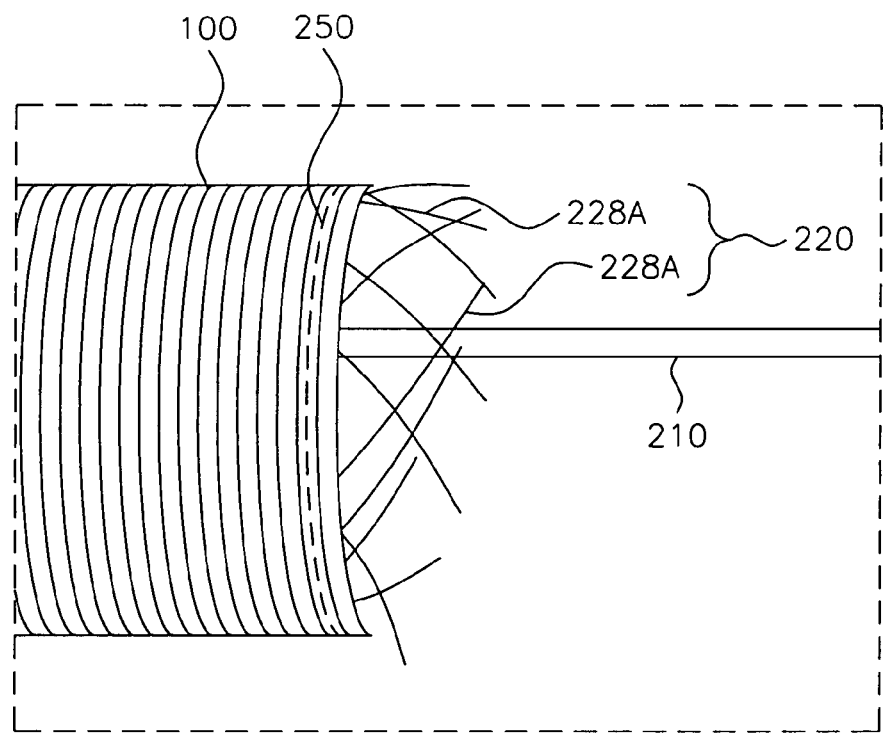
FIG. 10 shows a graft temporarily attached to a delivery or temporary stent according to an exemplary embodiment of the invention.
Figure 11:
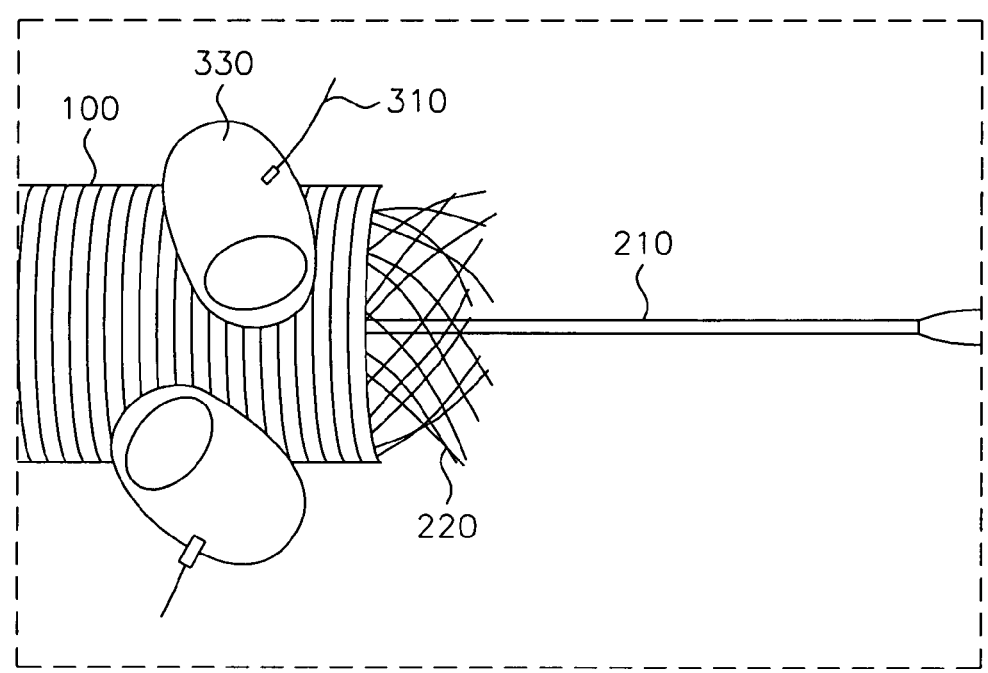
FIG. 11 shows a graft with permanent vessel fixation devices deployed while the graft is temporarily attached to a delivery or temporary stent according to an exemplary embodiment of the invention (with the vessel omitted for clarity)

Referring now to FIGS. 9-11, graft 100 is stabilized by temporary stent 220 fixed to a wall of a body lumen (e.g., a blood vessel, and particularly abdominal aorta 2). As shown in FIG. 10 discrete ends 228A of temporary stent 220 extend distally beyond graft 100. Discrete ends 228A (i.e., ends of thread members 222 that are not attached to each other, although they may overlap or cross each other at the discrete ends) are temporarily attached to graft 100. The outward expansion force of temporary stent 220 stabilizes graft 100 against aorta 2 spanning aneurysm 12, as shown in FIG. 9. While graft 100 is stabilized by temporary stent 220, a fixation structure, such as T-fastener 300, is used to attach graft 100 to aorta 2. T-fastener 300 comprises a tack 320 attached to an anchor line (i.e., suture) 310. A pledgette 330 is connected to anchor line 310 such that it can freely slide on the anchor line. Tack 320, which is shaped as an elongated cylinder, is driven through the wall of aorta 2 and graft 100 while its axis is oriented perpendicular to the surfaces of the aorta and graft. After tack 320 is inserted into aorta 2 and graft 100, anchor line 310 is drawn back so that tack 320 is pulled against the inner wall of graft 100 with its axis parallel to the inner surface of the graft. A crimp 340 is applied to anchor line 310 locking pledgette 330 against the outside surface of aorta 2 with anchor line 310 in tension. Aorta 2 and graft 100 are compressed between tack 320 and pledgette 330 fixing graft 100 to aorta 2, as shown in FIG. 9. In an exemplary embodiment of the invention, T-fastener 300 can be applied to fix graft 100 to aorta 2 using laparoscopic techniques. Alternative embodiments are contemplated in which alternate permanent fixation devices such as sutures or staples are used in place of T-fasteners and in which permanent fixation devices are introduced endovascularly or even using a combination of endovascular and laparoscopic techniques to introduce permanent fixation devices.

Following fixation of graft 100 to the wall of a blood vessel, sheath 230 is distally drawn over temporary stent 220 to reconstrain the temporary stent. Alternatively, temporary stent 220 may be proximally drawn into sheath 230 to reconstrain the temporary stent. Graft 100 is released from temporary stent 220 when discrete ends 228A of thread members 228 are drawn through temporary fixation devices 250 by the axial movement of temporary stent 220 with respect to fixed graft 100. Similarly, discrete ends 228A are drawn through permanent fixation devices, such as T-fasteners 300.

With temporary stent 220 constrained in sheath 230 and detached from temporary fixation devices 250 and T-fasteners 300, delivery device 200 may be proximally withdrawn from aorta 2 with minimum risk of trauma to the aorta.

As shown in FIG. 6, thread members 222 are sufficiently separated to allow blood flow through the temporary stent 220, when temporary stent 220 is expanded. Because temporary stent 220 and graft 100 are constrained during delivery or advancement of the graft blood can flow around them during deployment. After graft 100 is advanced to the location of an aneurysm, sheath 230 is drawn off of temporary stent 220 allowing temporary stent 220 to expand to stabilize graft 100, and allowing blood to flow through temporary stent 220. Accordingly, graft 100 may be delivered and stabilized at the aneurysm without interrupting blood flow in the vessel (e.g., abdominal aorta) having the aneurysm.

Delivery device 200 may optionally include an intravascular ultrasound device (not shown) attached to catheter 210 to provide visualization within the blood vessel. Visualization would facilitate precise placement of graft 100. Visualization would also be useful in verifying proper fixation.

Figure 12:
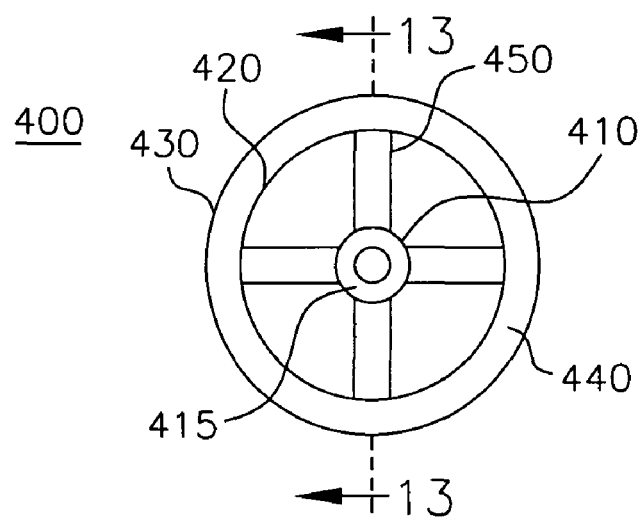
FIG. 12 shows a perfusion balloon for supporting a graft during permanent fixation according to an exemplary embodiment of the invention.
Figure 13:
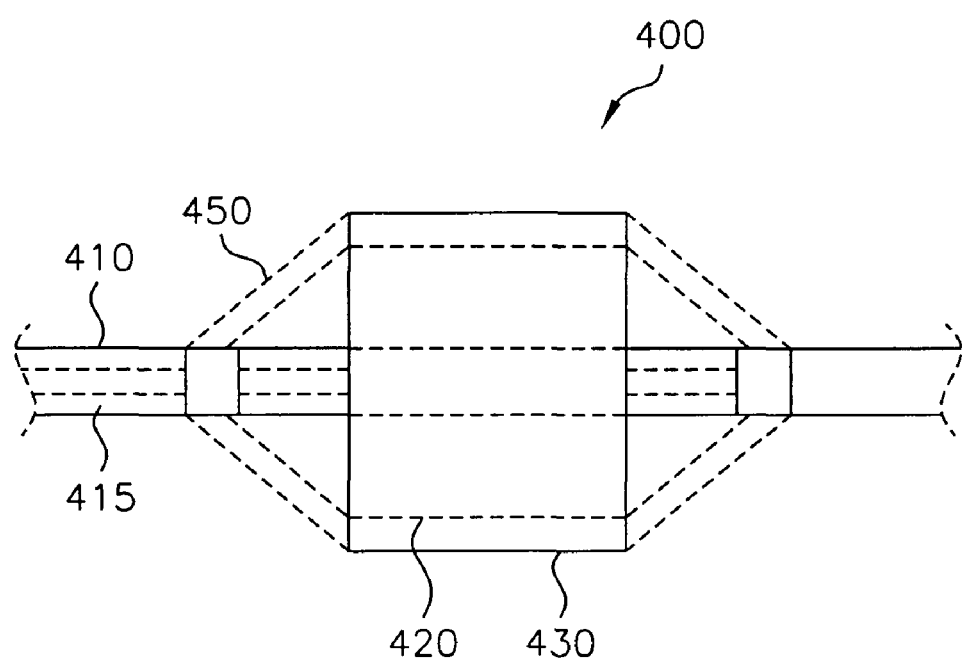
FIG. 13 shows a sectional view of the perfusion balloon of FIG. 12 taken generally along axis 13-13.

Following removal of delivery device 200, a balloon, such as a perfusion balloon 400, illustrated in FIGS. 12 and 13, may be intravascularly introduced to the location of graft 100 to support or stabilize the graft during surgical management of an aneurysmal sac. In an exemplary embodiment of the invention, perfusion balloon 400 stabilizes graft 100 while allowing blood flow through the perfusion balloon. A balloon catheter 410 is endovascularly advanced over guide wire 150 to aneurysm 12 and graft 100. Balloon catheter 410 includes an inflation lumen 415 through which an inflating fluid may be directed to an inflation cavity 440 of perfusion balloon 400. When the aneurysm sac is opened for sac management, a pressure change occurs on the graft, which can cause leakage between the graft and the aortic wall. Perfusion balloon 400 applies pressure to the graft in a radially outward direction, helping the graft to maintain a seal with the aortic wall when the aneurysm sac is opened.

Inflation cavity 440 is formed and bounded by an essentially cylindrical inner wall 420 and an essentially cylindrical outer wall 430. Inner wall 420 is surrounded by and sealed to outer wall 430 at each end to form inflation cavity 440 between inner wall 420 and outer wall 430. Inner wall and outer wall may be sealed, for example, with an adhesive, by solvent bonding, by laser welding, by ultrasonic welding, or by other techniques known in the art for joining two surfaces. Inner wall 420 has a first stiffness, and outer wall has a second stiffness, which is less than the first stiffness. These different stiffnesses may be provided by using different materials for inside wall 420 and outside wall 430 or by providing stiffening structures, such as ribs, to inside wall 420.

Inflation cavity 440 is in fluid communication with inflation lumen 415 through a plurality of inflation tubes 450 associated with perfusion balloon 400. Inflation tubes 450 extend radially outward from inflation catheter 410 and are spaced apart to allow blood flow between them. Inflation tubes 450 may be angled to form a generally frustoconical structure for stability when perfusion balloon 400 is inflated.

Because inside wall 420 is stiffer than outside wall 430, the pressure exerted by fluid in inflation cavity 440 causes outer wall 430 to expand more than inner wall 420 upon inflation. Thus, outer wall 430 expands radially outward to press against graft 100, while inner wall 420 remains spaced from catheter 410 when the inflation cavity is inflated. When perfusion balloon 400 is inflated blood flows between circumferentially spaced inflation tubes 450 into and through an open pathway between radially spaced catheter 410 and inner wall 420.

Figure 15:
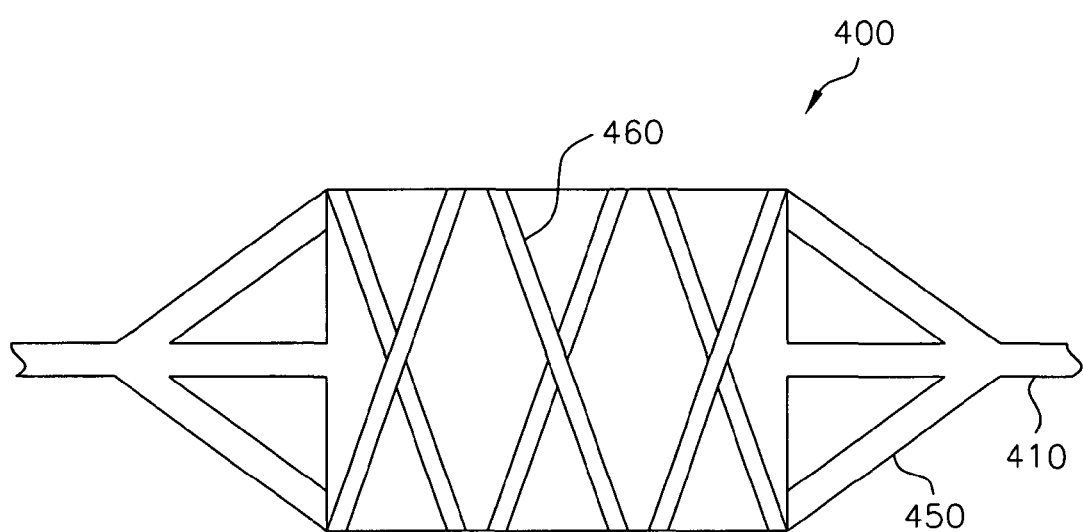
FIG. 15 shows a scaffold on a perfusion balloon according to an exemplary embodiment of the invention.

Perfusion balloon 400 may optionally include a scaffold 460 attached to outer wall 430, as shown in FIG. 15. Scaffold 460 provides increased structural rigidity to perfusion balloon 400, and may comprise a shape memory material or a stressed elastic material.

In an exemplary embodiment of the invention a method is provided for treating an aneurysm. The following description illustrates treatment of an abdominal aortic aneurysm. Treatment of other vessel defects and other aneurysms, such as a thoracic aortic aneurysm, however, are contemplated within the invention. An endovascular graft, such as graft 100, is configured to be disposed within an abdominal aorta 2 of a patient and to be attached to an aortic wall to channel aortic blood flow therethrough. Graft 100 is attached temporarily to a temporary stent 220, which is attached to catheter 210. Temporary stent 220 and catheter 210 (i.e., stent catheter) are part of a delivery device 200 as described herein. Graft 100 may be temporarily affixed to temporary stent 220 using, for example, sutures, adhesive, pockets formed in graft 100, or a ring encircling the temporary stent and graft.

Catheter 210 and graft 100 are advanced to a location of aneurysm 12 in aorta 2 (shown in FIG. 1). To advance catheter 210 and graft 100 to aneurysm 12, a cut down is performed in a patient's groin to surgically access the patient's iliac artery 4. Then, a guide wire 150 is introduced through iliac artery 4 and guided to the location of aneurysm 12, so that guide wire extends beyond or distal to aneurysm 12. Guide wire may, for example, be guided to aneurysm 12 by fluoroscopy. Catheter 210 is disposed on guide wire 150 such that it slides freely along the guide wire. Catheter 410 is then advanced endovascularly through iliac artery 4 and into aorta 2 from a position external to the patient's body.

While catheter 210 and graft 100 are advanced to aneurysm 12, graft 100 is temporarily attached to discrete ends 228A at distal end 228 of temporary stent 220, as described herein. Also, during advancement, temporary stent 220 and graft 100 are radially constrained by sheath 230, outer sheath 240, crochet rip cord 500 or a combination thereof. Optionally, a catheter-based intravascular ultrasound device may be used to provide visualization during advancement and subsequent fixation of graft 100.

When graft 100 is advanced to the portion of aorta 2 where aneurysm 12 is located, sheath 230 is drawn proximally off temporary stent 220 to allow the temporary stent to expand radially and stabilize the graft against the aortic wall. As described herein, temporary stent 220 is radially self-expanding due to its composition and structure. Graft 100 is pressed against the wall of aorta 2 both proximal and distal to aneurysm 12. Aortic blood flow is channeled into graft 100 and flows through gaps in temporary stent 220 between thread members 222.

With temporary stent 220 stabilizing graft 100, graft 100 is fixed to the wall of aorta 2. In an exemplary embodiment of the invention, graft 100 is fixed to the aortic wall using T-fasteners 300 or sutures. T-fasteners 300 or sutures may be introduced laparoscopically or endovascularly. T-fasteners 300 or sutures used to fix graft 100 to the aortic wall may capture discrete ends 228A of temporary stent 220, as shown in FIG. 9.

After graft 100 is fixed to the aortic wall, temporary stent 220 is reconstrained by sheath 230. This may be accomplished by drawing temporary stent 220 proximally into sheath 230 by urging catheter 210 proximally. Alternatively, sheath 230 may be urged distally to reconstrain temporary stent 220. Reconstraining temporary stent 220 causes a tension in discrete ends 228A of temporary stent 220, because they are pulled radially inward while graft 100 is fixed to the aortic wall. This tension, along with proximal movement of temporary stent 220 relative to graft 100, draws discrete ends 228A to a position proximal to T-fasteners 300 or sutures affixing graft 100 to temporary stent 220 (i.e., under tacks 320 or sutures). Discrete ends 228A are also withdrawn from (i.e., drawn proximal to) temporary attachment devices 250, releasing the fixated graft 100.

After temporary stent 220 is reconstrained by sheath 230, temporary stent 220, sheath 230, and catheter 210 are withdrawn from the aorta 2 through the iliac artery 4 and out of the patient's body. Because temporary stent 220 is constrained, it can be withdrawn without causing trauma to the blood vessels through which it passes.

In an exemplary embodiment, following fixation of the graft to the aortic wall and reconstraining the temporary stent, the temporary stent is repositioned at the proximal end of the graft and redeployed to stabilize the proximal end of the graft against the aortic wall. The proximal end of the graft is fixed to the aortic wall using one of the fixation devices described above. Then the temporary stent is reconstrained and removed from the body.

When the graft is a bifurcated graft, the stent may also be redeployed in each of the iliac branches for fixation of the bifurcated legs of the graft.

After delivery device 200 is removed from the patient, a perfusion balloon 400, as described herein, may be introduced to the area of aneurysm 12 on guide wire 150. Perfusion balloon 400 is attached to a balloon catheter 410 by a plurality of inflation tubes 450. Inflation tubes 450 are spaced to allow blood flow between them and into and through an opening between inner wall 420 of inflation balloon 400 and balloon catheter 410 when perfusion balloon 400 is inflated. Perfusion balloon is deflated during advancement to aneurysm 12 to allow easier passage through blood vessels.

When perfusion balloon 400 is advanced into graft 100, it is inflated by directing fluid through inflation lumen 415 in balloon catheter 410, into and through inflation tubes 450, and into inflation cavity 440. Because inner wall 420 is stiffer than outer wall 430, outer wall expands to press against graft 100 stabilizing graft 100 against the aortic wall, while inner wall 420 remains separated from balloon catheter 410.

With perfusion balloon 400 stabilizing graft 100, the sac formed by aneurysm 12 is surgically managed. For example, the sac may be opened and drained. Sac management may be performed laparoscopically using existing laparoscopic scissors, graspers, and suction tools. Because perfusion balloon 400 is stabilizing graft 100, endoleaks associated with pressure and shape changes from sac rupture are reduced. Sac management also reduces the need for medical follow-up to monitor sac morphology.

Sutures, clips, or the like may be used to seal any exposed feeder arteries to the sac. The sac is then wrapped around graft 100 and sealed upon itself. Excess tissue may be trimmed off as necessary. Perfusion balloon 400 is then deflated and removed from the patient's body by drawing balloon catheter 410 out through iliac artery 4.

In an alternative exemplary embodiment, temporary stent 220 does not expand due to elasticity or shape memory of thread members 222. Instead, helically braided thread members 222 are expanded radially outwardly to a maximum diameter in a resting state by an expansion mechanism. The expansion mechanism may be, for example, a perfusion balloon. In an exemplary embodiment temporary stent 220 has a radially expanded resting state and a radially compressed resting state. The radially expanded resting state, as shown in FIG. 6, is for attachment of graft 100 to lumen walls. The radially compressed resting state, similar in dimension to a constrained state, is for delivery of graft 100 and removal of temporary stent 220. In this exemplary embodiment, temporary stent 220 may be fastened to a perfusion balloon. The perfusion balloon is deflated such that the temporary stent 220 is in the radially compressed resting state for advancement to the graft location. At the graft location, the perfusion balloon is inflated, causing the temporary stent to expand to the radially expanded resting state. After fixation of the graft 100, the balloon is deflated, causing the temporary stent to return to the radially compressed resting state for removal from the body.

In another alternative exemplary embodiment, temporary stent 220 is self-closing to a radially compressed resting state. In this embodiment, the self-closing temporary stent remains on a perfusion balloon during advancement to a graft location due to friction. The temporary stent and the graft are expanded at the graft location by inflation of the perfusion balloon. Following fixation of the graft, the perfusion balloon is deflated allowing the self-closing temporary stent to return to the radially compressed resting state for removal from the body.

Although illustrated and described above with reference to certain specific embodiments, the present invention is nevertheless not intended to be limited to the details shown. Rather, various modifications may be made in the details within the scope and range of equivalents of the claims and without departing from the invention.

In an exemplary alternate embodiment, a temporary stent may be used to deliver a graft to a thoracic aortic aneurysm, or to deliver a graft to another vascular location to treat an aneurysm or other vascular condition. A thoracic aortic aneurysm may be accessed for example, by introducing a temporary stent and temporarily attached graft through an iliac artery, the lower aorta, an inominate artery, a carotid artery, a pulmonary artery, or a subclavian artery. The temporary stent and graft may be introduced through an open surgical procedure or through a laparotomy.

What is claimed:

1. A method of treating an abdominal aortic aneurysm, the method comprising the steps of:
   providing an endovascular graft configured to be disposed within an aorta of a patient and to be attached to an aortic wall to channel aortic blood flow therethrough;

advancing a temporary stent catheter endovascularly to a location of the aneurysm, the catheter being attached to a temporary stent, the temporary stent being generally tubular and having a distal end and a proximal end and comprising outwardly expanding helically braided thread members, the temporary stent being tapered and affixed to the catheter at the proximal end and terminating in discrete ends temporarily affixed to the graft at the distal end, the temporary stent and the graft being constrained by one or more constraining devices during advancement of the graft;

removing the one or more constraining devices from the graft and temporary stent, to allow the temporary stent to stabilize the graft against the aortic wall;

fixing the graft to the aortic wall;

reconstraining the temporary stent with one of the one or more constraining devices; and withdrawing the temporary stent catheter, temporary stent and the one or more constraining devices, releasing the graft.

2. The method of claim 1 wherein one of the one or more restraining devices is a sheath and the temporary stent is reconstrained by proximally drawing the temporary stent into the sheath.

3. The method of claim 1 wherein one of the one or more restraining devices is a sheath and the temporary stent is reconstrained by distally advancing the sheath over the temporary stent.

4. The method of claim 1 wherein the graft is fixed to the aortic wall endovascularly.

5. The method of claim 4 further comprising, following the step of fixing the graft to the aortic wall, the step of:
surgically opening the aneurysm sac.

6. The method of claim 1 wherein the graft is fixed to the aortic wall laparoscopically.

7. The method of claim 1 wherein aorta is surgically opened and the graft is fixed to the aortic wall after surgically opening the aorta.

8. The method of claim 7 wherein the graft is fixed to the aortic wall using sutures.

9. The method of claim 7 wherein the graft is fixed to the aortic wall using T-fasteners.

10. The method of claim 1 wherein the graft is temporarily fixed to the temporary stent using sutures.

11. The method of claim 1 wherein the graft is temporarily fixed to the temporary stent using an adhesive.

12. The method of claim 1 wherein the graft is temporarily fixed to the temporary stent using a ring encircling the graft and temporary stent.

13. The method of claim 1 wherein the graft comprises pockets and the graft is temporarily fixed to the temporary stent by fitting the discrete end of the thread members in the pockets during advancement of the temporary stent catheter.

14. The method of claim 1 further comprising, prior to advancing the temporary stent catheter, the steps of:
performing a cut down in a patient's groin to surgically access the patient's iliac artery; and
introducing a guide wire through the iliac artery to a location in the aorta distal the aneurysm;
wherein the temporary stent catheter is disposed on the guide wire.

15. The method of claim 1 further comprising the steps of:
advancing a balloon catheter over the guide wire to the location of the aneurysm; the perfusion balloon catheter attached to a perfusion balloon by a plurality of inflation tubes spaced to allow blood flow therebetween;

inflating the perfusion balloon via the inflation tubes to stabilize the graft;
surgically managing a sac formed by the abdominal aortic aneurysm;
deflating the perfusion balloon; and
withdrawing the balloon catheter and perfusion balloon through the iliac artery.

16. The method of claim 15 wherein the sac is surgically treated while the perfusion balloon stabilizes the graft.

17. The method of claim 1 wherein a catheter-based intravascular ultrasound device is used to provide visualization during fixation of the graft.

18. The method of claim 1 further comprising the step of:
endovascularly sealing inferior mesenteric and lumbar arteries.

19. The method of claim 1 wherein the one or more constraining devices comprise a sheath constraining the temporary stent and the graft during advancement of the graft.

20. The method of claim 1 wherein the one or more constraining devices comprise a sheath constraining the temporary stent and an outer sheath constraining the graft during advancement of the graft.

21. The method of claim 1 wherein the one or more constraining devices comprise a sheath constraining the temporary stent and crochet constraining the graft during advancement of the graft.

22. The method of claim 1 further comprising, following the step of reconstraining the temporary stent, the steps of:
repositioning the temporary stent at the proximal end of the graft;
deploying the temporary stent to stabilize the proximal end of the graft against the aortic wall;
fixing proximal end of the graft to the aortic wall; and
reconstraining the temporary stent with one of the one or more constraining devices.

23. The method of claim 22 wherein the graft is a bifurcated graft and the method further comprises, following the second reconstraining step, the steps of:
repositioning the temporary stent at the distal end of the transverse leg of the bifurcated graft;
deploying the temporary stent to stabilize the distal end of the transverse leg of the bifurcated graft against the aortic wall;
fixing the distal end of the transverse leg of the bifurcated graft; and
reconstraining the temporary stent with one of the one or more constraining devices.

24. A method of treating a thoracic aortic aneurysm, the method comprising the steps of:
providing an endovascular graft configured to be disposed within an aorta of a patient and to be attached to an aortic wall to channel aortic blood flow therethrough;
advancing a temporary stent catheter endovascularly to a location of the aneurysm, the catheter being attached to a temporary stent, the temporary stent being generally tubular and having a distal end and a proximal end and comprising outwardly expanding helically braided thread members, the temporary stent being tapered and affixed to the catheter at the proximal end and terminating in discrete ends temporarily affixed to the graft at the distal end, the temporary stent and the graft being constrained by one or more constraining devices during advancement of the graft;
drawing the one or more constraining devices off of the graft and the temporary stent to allow the temporary stent to stabilize the graft against the aortic wall;
fixing the graft to the aortic wall;

reconstraining the temporary stent with one of the one or more constraining devices; and withdrawing the temporary stent catheter, temporary stent and constraining devices, releasing the graft.

25. The method of claim 24 wherein one of the one or more constraining devices is a sheath and the temporary stent is reconstrained by proximally drawing the temporary stent into the sheath.

26. The method of claim 24 wherein one of the one or more constraining devices is a sheath and the temporary stent is reconstrained by distally advancing the sheath over the temporary stent.

27. The method of claim 24 wherein the graft is fixed to the aortic wall endovascularly.

28. The method of claim 24 wherein the graft is fixed to the aortic wall laparoscopically.

29. The method of claim 28 wherein the graft is fixed to the aortic wall using sutures.

30. The method of claim 28 wherein the graft is fixed to the aortic wall using T-fasteners.

31. The method of claim 24 wherein the graft is temporarily fixed to the temporary stent using sutures.

32. The method of claim 24 wherein the graft is temporarily fixed to the temporary stent using an adhesive.

33. The method of claim 24 wherein the graft is temporarily fixed to the temporary stent using a ring encircling the graft and temporary stent.

34. The method of claim 24 wherein the graft comprises pockets and the graft is temporarily fixed to the temporary stent by fitting the discrete ends of the thread members in the pockets during advancement of the temporary stent catheter.

35. The method of claim 24 further comprising, prior to advancing the temporary stent catheter, the steps of:

performing a cut down in a patient's groin to surgically accessing the patient's femoral artery; and introducing a guide wire through the femoral artery to a location in the aorta distal the aneurysm;

wherein the temporary stent catheter is disposed on the guide wire.

36. The method of claim 24 wherein a catheter-based intravascular ultrasound device is used to provide visualization during fixation of the graft.

37. The method of claim 24 further comprising, following the step of reconstraining the temporary stent, the steps of:

repositioning the temporary stent at the proximal end of the graft;

deploying the temporary stent to stabilize the proximal end of the graft against the aortic wall;

fixing proximal end of the graft to the aortic wall; and reconstraining the temporary stent with one of the one or more constraining devices.

38. A method of treating a luminal defect aneurysm, the method comprising the steps of:

providing an endoluminal graft configured to be disposed within a body lumen of a patient and to be attached to a luminal wall to channel fluid flow therethrough;

advancing a temporary stent catheter endoluminally to a location of the defect, the catheter being attached to a temporary stent, the temporary stent having a radially expanded configuration and a radially compressed configuration and comprising helically braided thread members, the temporary stent terminating in discrete ends temporarily affixed to the graft, the temporary stent being in the radially compressed configuration during advancement of the graft;

expanding the sheath to the radially expanded configuration to stabilize the graft against the luminal wall;

fixing the graft to the luminal wall;

constraining the temporary stent to release the graft; and withdrawing the temporary stent catheter and temporary stent from the patient.

39. The method of claim 38 wherein the temporary stent is constrained by proximally drawing the temporary stent into a sheath.

40. The method of claim 38 wherein the temporary stent is constrained by distally advancing a sheath over the temporary stent.

41. The method of claim 38 wherein the graft is fixed to the luminal wall endovascularly.

42. The method of claim 38 wherein the graft is fixed to the luminal wall laparoscopically.

43. The method of claim 42 wherein the graft is fixed to the luminal wall using sutures.

44. The method of claim 42 wherein the graft is fixed to the luminal wall using T-fasteners.

45. The method of claim 38 wherein the graft is temporarily fixed to the temporary stent using sutures.

46. The method of claim 38 wherein the graft is temporarily fixed to the temporary stent using an adhesive.

47. The method of claim 38 wherein the graft is temporarily fixed to the temporary stent using a ring encircling the graft and temporary stent.

48. The method of claim 38 wherein the graft comprises pockets and the graft is temporarily fixed to the temporary stent by fitting the discrete ends of the thread members in the pockets during advancement of the temporary stent catheter.

49. The method of claim 38 further comprising, prior to advancing the temporary stent catheter, the steps of:

performing a cut down in a patient's groin to surgically accessing the patient's femoral artery; and introducing a guide wire through the femoral artery to a location in the aorta distal the aneurysm;

wherein the temporary stent catheter is disposed on the guide wire.

50. The method of claim 38 wherein a catheter-based intravascular ultrasound device is used to provide visualization during fixation of the graft.

* * * * *